(12) United States Patent
Schwarz (10) Patent No.: US 9,629,810 B2
(45) Date of Patent: Apr. 25, 2017

(54) CAPSULE WITH SOLUBLE BLOCKING ELEMENT

(75) Inventor: Franz Xaver Schwarz, Worgl (AT)

(73) Assignee: SANDOZ AG, Basel (CH)

( * ) Notice: Subject to any disclaimer, the term of this patent is extended or adjusted under 35 U.S.C. 154(b) by 1149 days.

(21) Appl. No.: 13/063,045

(22) PCT Filed: Sep. 9, 2009

(86) PCT No.: PCT/EP2009/061670
§ 371 (c)(1),
(2), (4) Date: Apr. 1, 2011

(87) PCT Pub. No.: WO2010/029095
PCT Pub. Date: Mar. 18, 2010

(65) Prior Publication Data
US 2011/0174653 A1  Jul. 21, 2011

(30) Foreign Application Priority Data

Sep. 10, 2008 (EP) .................................. 08164093
May 8, 2009 (EP) .................................. 09159784

(51) Int. Cl.
*A61K 9/48* (2006.01)
*A61M 15/00* (2006.01)
(Continued)

(52) U.S. Cl.
CPC ............. *A61K 9/4808* (2013.01); *A61J 3/071* (2013.01); *A61M 15/0016* (2014.02);
(Continued)

(58) Field of Classification Search
CPC .......... A61M 15/0001; A61M 15/0016; A61M 15/0028; A61M 15/003; A61M 15/0031;
(Continued)

(56) References Cited

U.S. PATENT DOCUMENTS 4,981,468 A * 1/1991 Benefiel et al. ................ 604/83
5,221,278 A * 6/1993 Linkwitz et al. .......... 604/890.1
(Continued)

FOREIGN PATENT DOCUMENTS

DE  202006019749 U1  4/2008
WO  9703634 A  2/1997
(Continued)

OTHER PUBLICATIONS

International Search Report (completed Jun. 21, 2010).
(Continued)

*Primary Examiner* — Imani Hayman
*Assistant Examiner* — Larry R Wilson
(74) *Attorney, Agent, or Firm* — Jeffrey S. Melcher; Manelli Selter PLLC (57) ABSTRACT

The invention relates to a capsule comprising an inlet and an outlet connected by a passage, in which a dissolvable blocking element and a composition to be orally administered are arranged. The blocking element is fluid permeable and, in a non-dissolved condition, is arranged in the passage to block delivery of the composition to an outlet of the passage. The invention further relates to a method for releasable sealing a capsule comprising a composition to be orally administered, comprising the steps of providing the composition chamber in a passage and filling composition into the composition chamber. The passage formed by the capsule is occluded with a blocking element and the blocking element comprises dissolvable material and has a fluid permeable structure.

9 Claims, 3 Drawing Sheets

(51) Int. Cl.
*A61J 3/07* (2006.01)
*A47G 21/18* (2006.01)
*A61J 7/00* (2006.01)

(52) U.S. Cl.
CPC .... *A61M 15/0028* (2013.01); *A61M 15/0043* (2014.02); *A47G 21/18* (2013.01); *A47G 21/183* (2013.01); *A61J 7/0038* (2013.01)

(58) Field of Classification Search
CPC ............ A61M 15/0043; A61M 15/0046; A61J 3/071; A61J 3/072; A61J 7/0038; A61J 15/0011; A47G 21/18; A47G 21/183; A47G 2400/027; A61K 9/0004; A61K 9/0056; A61K 9/006; A61K 9/0073; A61K 9/4808
USPC ..... 604/167.01, 236–238, 288, 890.1, 891.1, 604/892.1, 77–79
See application file for complete search history.

(56) References Cited

U.S. PATENT DOCUMENTS

| | | | | |
|---|---|---|---|---|
| 5,780,058 A | * | 7/1998 | Wong et al. | 424/473 |
| 5,997,527 A | * | 12/1999 | Gumucio et al. | 604/892.1 |
| 6,096,003 A | * | 8/2000 | Wong | A47G 21/183 604/78 |
| 2003/0087005 A1 | * | 5/2003 | Baron | 426/85 |
| 2003/0143257 A1 | * | 7/2003 | Fleshner-Barak | A61K 9/2072 424/426 |
| 2005/0106188 A1 | * | 5/2005 | Sedaghat Kerdar et al. | 424/400 |
| 2010/0121315 A1 | * | 5/2010 | Trovato et al. | 604/890.1 |
| 2010/0168663 A1 | * | 7/2010 | Maury | 604/77 |

FOREIGN PATENT DOCUMENTS

| | | |
|---|---|---|
| WO | 200400202 A | 12/2003 |
| WO | 2004000202 A | 12/2003 |
| WO | 2004000203 A | 12/2003 |
| WO | 2008036885 A2 | 3/2008 |

OTHER PUBLICATIONS

International Preliminary Report on Patentability (mailed Dec. 22, 2010).
European Search Report.

* cited by examiner

CAPSULE WITH SOLUBLE BLOCKING ELEMENT

CROSS-REFERENCE TO RELATED APPLICATIONS

This application is a national stage entry under 35 U.S.C. 371 of International Application No. PCT/EP2009/061670, filed 9 Sep. 2009, designating the United States. This application claims foreign priority under 35 U.S.C. 119 and 365 to European Patent Application Nos. 08164093.0, filed 10 Sep. 2008, and 09159784.9, filed 8 May 2009.

TECHNICAL FIELD OF THE INVENTION

The present invention relates to oral application of substances, a device for the oral application of substances and a method for filling the device.

TECHNICAL BACKGROUND

Oral administration or application of pharmaceutical formulations comprising an active pharmaceutical ingredient with an unpleasant taste remains a technical challenge. In particular, children show a very bad compliance towards bitter formulations. Taste masked formulations have been developed to improve patient compliance.

However, taste-masked formulations typically only work well for solid dosage forms. If liquid drug mixtures are used or in the case of high doses, i.e. large amounts of substance to be swallowed, taste-masked formulations typically do not work satisfactory.

In WO 97/03634, a delivery system for the oral application of a formulation is described, in which a formulation chamber comprises the formulation retained by a retainer. The device described therein is a pipe forming a chamber, which is sealed by cap and a plug moveable within the pipe. For oral application, one end of the pipe—the inlet—is immersed in liquid, while the other end—the outlet—is applied to the patient's mouth. Comparable to the use of a straw, the patient draws the drink into the pipe and the device allows a fluid to flow through the pipe, while the agent formulation is carried away together with the drink flowing through the pipe. For both, filling of the pipe with the formulation to be administered and emptying of the pipe by the patient, the same end—i.e. the outlet—is used. Further, the moveable plug moves through the pipe together with the flow entering into the pipe. Both ends of the pipe are crimped for preventing the release of the moveable plug.

For consummation, a cap has to be removed from one end in order to enable the active agent to be drawn through the opened end. In particular in case of incorrect use, for example by tilting or shaking the pipe, at least a part of the active agent can be lost.

Other prior art systems also relate to pipes comprising a composition to be administered as well as a shiftable block element, which is shifted when the composition is applied. Other solutions provide elements, which are deformed by water (without being dissolved) for releasing an agent from a chamber. Another group of solutions is based on a grid-like blocking element, which holds back the composition to be administered, until the complete composition is dissolved and can be transported through the grid. Finally, systems are known comprising a blocking element which can be removed by hand before use.

Firstly, these systems all suffer from the disadvantage described above, i.e. the release of the composition before the administration to a patient involving the risk of losing a part of the active agent. This falsifies the dose provided to the patient. As a second disadvantage, all delivery systems provide both, a chamber for the composition to be administered as well as means for transporting the composition (distributed within a liquid) to the patient's mouth. In known systems for oral delivery the function of storing and delivering the composition (more exactly: the composition together with the liquid), the dimensions of the systems cannot be scaled down. Beyond a certain minimum dimension, the operation and handling of the system is difficult, which establishes an inherent limit for minimizing the dimensions and an inherent limit to the packaging density. For example, if the length of the pipe is less than 3 cm, it is difficult for a person to move the delivery system to a glass filled with a drink and, at the same time, introducing the other end of the delivery system into the mouth. Since the delivery system is provided for exactly one application rate, packages with a number of dosages become large, and by far larger than packages of other pharmaceutical products. If a package is required to cover one month of a pharmaceutical substance, which has to be administered twice per day, the package size is not comparable with package sizes of the same product in another form.

As a further important disadvantage, conventional delivery systems comprise a relatively complex mechanism, related to high manufacturing costs and a high amount of waste. For example the system of WO 97/03634 comprises as individual elements at minimum (1) a pipe (2) a plug movable within the pipe (3) crimped stoppers at each end of the pipe, (4) a cap and (5) the formulation between plug and cap. This relatively complex system is connected with a complex and costly manufacturing process. All of these elements are special components and are particularly designed for this purpose. In particular, the amount of waste is highly increased in comparison to other common application form like tablets.

It is therefore an object of the invention to provide a device and a process for administering a pharmaceutical substance, which requires low manufacturing costs and provides a higher package density.

SUMMARY OF THE INVENTION

This object is solved by the capsule and the manufacturing method according to the independent claims.

The underlying concept of the invention is to release a composition to be administered from a simple delivery system provided by a capsule by dissolving a dissolvable blocking element, which is located in the capsule, together with the composition. According to the invention, an oral delivery system is based on a capsule as a container for a composition, which needs to be administered. The capsule provides both, a storage space for the composition as well as a blocking/releasing element within the capsule. Since the capsule is suited for being combined with a delivery device like extension conduit or additional mouthpiece and does not comprise the delivery device itself, the space occupied by the capsule, in relation to the space occupied by the composition contained therein, is by far smaller than the space occupied by a device of the prior art containing the same amount of composition.

The concept underlying the invention is implemented by using a dissolvable blocking element in a capsule which allows (1) storage of medications, (2) manufacture at low costs, (3) application of known manufacturing processes, devices and components, which can be easily obtained, (4)

substantial reduction of waste and packaging, (4) drawing liquid through the passage by using a fluid permeable (pressure balancing) blocking element and (5) releasing composition upon contact of the blocking element with liquid drawn through the passage just in time, for example by dissolving upon contact with the liquid.

By the use of a capsule, in particular pharmaceutical capsules commonly known to drugmakers, commonly used components can be used as starting point for realizing the invention. In contrast to the prior art techniques, in which storage space and delivering component a provided by the identical component, the present invention combines all necessary functions (storage/release control) in a capsule, while a simple pipe (e.g. in form of a straw) is (re-)used into which the capsule is inserted for administering the composition from the capsule to the patient. In contrast to the prior art, in which the space filled by the devices is relatively large as compared to the amount of composition, the space taken by the inventive capsule is effectively used. In particular, the overhead of unused space in the prior art is a result of the delivering component (as integral part of the delivery device). Since the invention distinguishes between storing and releasing component (the inventive capsule) and the delivery device (an additional straw), the packaging density achieved with the invention is significantly higher than the maximum packaging density provided by prior art delivery devices, e.g. straws with a compartment for a composition.

In the same way the invention increases the packaging density and reduces the complexity of the capsule, the amount of waste connected to the delivery of one dose is significantly reduced. In particular, the device for transferring the composition from the capsule to the patient's mouth (a mouth piece or extension conduit) can be reused for a number of capsules/doses, even without disadvantages concerning hygiene.

The structure of the inventive capsule is compatible with and partly corresponds to widely used pharmaceutical capsules. Only a very simple modification of known capsules is necessary to realize the invention. For example, known pharmaceutical capsules (which are suited to be swallowed at once) can be provided with two openings (one at each capsule part) and, during a conventional step of combining both capsule parts, a dissolving blocking element is added. Even the step of adding the dissolving blocking element can be realized by machines commonly used to fill pharmaceutical capsules.

Eventhough the invention can be realized by only slightly modifying known pharmaceutical capsules and the corresponding manufacturing method, this modification according to the invention allows to use pharmaceutical capsules for a purpose, which fundamentally differs from the known use of pharmaceutical capsules. In contrast to the known use, i.e. delivering a formulation at once, together with the capsule by swallowing the filled capsule, the invention provides a way to deliver a formulation without the capsule and automatically distributed within a liquid. This inventive delivery method allows to deliver the pharmaceutical formulation together with the liquid (wherein the liquid can be used for taste masking) and to deliver the pharmaceutical formulation directly to the gastrointestinal tract for immediate ingestion, in contrast to a closed capsule used within the prior art, which releases the formulation only after chemical/physical removal of a part of the capsule.

In contrast to the prior art, the inherent properties of the oral delivery system according to the invention adequately address situations occurring in prior art systems, during which the composition is released (the tube is opened and the cap is removed) but the delivery operation is not carried out. In other words, with the present invention, there is no necessary time gap (during which composition material could be spilled) between opening the space containing the composition and using capsules. With the capsules according to the invention, the risk to loose a part of the composition by tilting or shaking a container after the cap has been removed is minimized.

As a particular advantage over the prior art, the invention can be realized and packaged in the same way, known pharmaceutical capsules are provided. This allows a very high packaging density. For example if compared to the device of WO 97/03634, which also includes a pipe and other components, the invention allows to increase the packaging density by a factor of 5 or more. In particular, commonly used packaging systems can be used; no complex adoptions to given packaging systems have to be carried out for realizing the invention. In addition, all prerequisites for realizing the invention (in particular pharmaceutical capsules) are known and approved to therapeutic goods regulations. This significantly reduces any studies to be carried out as prerequisite for marketing the inventive capsule.

Regarding material, shape, dimensions, surface and chemical/physical properties, the inventive capsule corresponds to known pharmaceutical two-part capsules, except for the openings and the dissolvable blocking element. The part of the capsule defining the passage (except for the openings) and the part of the capsule supporting the dissolvable blocking element are parts of a pharmaceutical capsule also used for providing a pharmaceutical formulation in form of capsule walls completely enclosing a composition. The capsule used within the invention is a two-part pharmaceutical capsule, which is modified by adding an opening to each of the two parts (in particular: the respective ends of the parts) providing the capsule. The inventive capsule is provided by a two-part pharmaceutical capsule, each part of which has been modified from a blind hole to a through boring. As a consequence of the inventive modification of a known pharmaceutical capsule, a (dissolvable) blocking element is provided for controllably retaining the composition within the capsule. In addition, a retainer is provided for holding the composition within the capsule. Blocking element and retainer replace the removed (closed) ends of the capsule parts, when the composition is stored within the capsule. For releasing the composition, the blocking element is activated, which is enabled by the openings resulting from the closed ends.

The capsule according to the invention is suited for storing the composition (similar to known pharmaceutical capsules) and for controlling the release of the composition according to an external event (introducing water into the capsule). The release control is provided by the openings and the blocking element, the openings allowing water to enter the capsule and the blocking element releasing the composition upon contact with water.

In order to release the composition and to remove the blocking element, the capsule comprises two open ends, i.e. two openings at opposed ends of the capsule. The capsule comprises a section with a substantially constant cross section (apart from connection elements and other), and connects two opposed end sections, in which the inner diameter tapers. As capsules, conventional capsules for medical use can be used, which are opened at both ends by removing small sections of the capsule's wall at opposed ends of the capsule. For providing the openings, a conventional capsule is cut or drilled, which provides openings used as inlet and outlet, the inlet being located opposed to the outlet. Preferably, the capsule (like conventional capsules) is provided in two parts as an inlet part and an outlet part, which are connected with each other, for example, by engaging, after the composition (and in case other components) is filled in.

According to the invention, the connection of both parts is a step of a manufacturing method, which can be realized by conventional capsule preparation devices. The manufacturing process of the inventive capsule can be provided by a number of conventional steps as well as by steps, which can be provided with minimal effort and can be realized by simple mechanisms. The method comprises: providing an inlet part as well as an outlet part. The opening providing the inlet and the outlet can be realized by providing the capsule parts which already comprise openings, or can be provided by opening (cutting, drilling or other removing techniques) a section of the tapered section of each capsule part. Instead of cutting, holes can be drilled. Preferably, at least one of the openings providing the inlet and/or the outlet has or have a diameter, which is significantly smaller than the inner diameter or the corresponding cross section of an inner section of the capsule, which connects the tapered section of the capsule. In this way, shoulders are formed as protrusions towards the passage formed by the capsule at the inlet and/or outlet sections. These shoulders provide stoppers or securing elements for the blocking element and/or for a retaining element in order to prevent the blocking element and/or the retaining element from being erroneously removed from the inside of the capsule to the outside of the capsule's wall or outside the passage (or the inlet and outlet, respectively). The method further comprises introducing a dissolvable element as a blocking element, filling a composition in form of particles into the capsule and closing the space, in which the composition is located by adding an insoluble filter, grid, or other retaining element to the capsule. Finally, both parts are put together, for example, by engaging, snap fit or press-fit. Generally, the parts can also be connected with each other by form-fit, force-fit or other types of mechanical connection. After the manufacturing process, the composition is held between the retaining element and the blocking element as well as by one part (or by both parts) of the capsule. As capsule, conventional gelatin capsules can be used and, consequently, the conventional devices for preparing the capsules can be used. In one embodiment, the capsule's wall is made of a composition comprising methylcellulose or hydroxypropyl methyl cellulose (HPMC) or both. As material for forming the capsule, elastic material is preferred to allow press-fit of other components or between the two parts forming the capsule. The capsule can be comprised of the blocking element's material, however in a form with a substantially decreased surface density for ensuring a substantially faster dissolving of the blocking element in comparison to the capsule. In another embodiment, the capsule is provided of a material having an insoluble surface layer covering the inner and/or the outer surface of the capsule. As material for providing the capsule, any material is suitable that does not affect the human body upon contact and that does not react adversely with the composition to be stored, e.g. natural or synthetic polymers formed as continuous layers.

Preferably, the composition to be administered comprises at least one active agent, e.g. a pharmaceutical substance. Since the oral administration is accompanied by a liquid flow carrying the composition to be administered, or, in short form, the composition, the liquid can be used to dissolve a blocking element, which blocks the composition in the delivery system before use and releases the composition if liquid is drawn through a passage, for example a tube. Thus, the passage of the capsule according to the invention, together with the capsule, fulfils the following functions: storing the composition before use, whereby the blocking element blocks the passage before use; directing the liquid flowing through the composition and supporting the dissolvable blocking element such that the liquid can come into contact with the blocking element and dissolve the blocking element of the capsule. Correspondingly, the blocking element has the following functions: keeping the composition stored in the passage, i.e. within the capsule, before use of the capsule and allowing the release of the composition when the blocking element comes into contact with a liquid drawn through the capsule, i.e. through the interior of the capsule passage. Thus, the passage provided by the capsule is made permeable to the active agent, for example by dissolving the blocking element, thereby clearing the passage. In this way, before use the dissolvable blocking element separates the space, in which the composition is stored in the capsule's passage, from an outlet of the capsule. Upon delivery, the dissolvable blocking element is made permeable to the active agent, for example by disappearing as (partly or completely) dissolved material in the flow. This releases the composition from the capsule just in time during the delivery operation. Since delivery is linked to the operation of drawing liquid through the capsule, the release of the composition is automatically triggered by the start of the delivery operation.

The dissolved blocking element may as a further advantage also contribute to taste masking of the pharmaceutical composition to be delivered to a patient. Thus, the material or a material component of the blocking element preferably comprises a flavor additive. Alternatively or in combination thereto, the blocking element forms or comprises a structure which releases flavor additive when the blocking element is brought into contact with liquid solvent, in particular upon contact with water or an aqueous solution. The flavor additive is released upon dissolving at least parts of the blocking element, by dissolving at least parts of the flavor additive, or a combination thereof.

Therefore, according to one aspect of the invention, a capsule is provided having a passage, in which a blocking element blocks the delivery of a composition stored in the passage. According to the invention, the capsule comprises two parts connected with each other, as well as an inlet and an outlet connected by the capsule's passage. Further, the blocking element is, in an non-dissolved condition, fluid permeable and allows to draw liquid, for example water or suitable aqueous compositions, into the passage. The dissolvable blocking element, which is arranged in the passage, is adapted to allow release of the composition upon contact with the liquid, since the blocking element is dissolvable in said liquid, in particular in water or suitable aqueous compositions such as juice or other drinks. The blocking element can be arranged nearby the outlet of the passage, or nearby the inlet. This position enables the blocking element to become dissolved upon immersing at least a part of the oral delivery system in liquid.

According to a first aspect of the invention, the composition is held back from the outlet, for example by being arranged between the blocking element and a retainer in the capsule, for example an non-dissolvable fluid-permeable filter. In this way, the composition may be sandwiched between the blocking element and the retainer and can be released, if the blocking element is dissolved.

According to a second aspect of the invention, the composition and the blocking element within the capsule are at least partly coextensive such that the composition is at least partly supported in the structure of the blocking element. In other words, the blocking element forms a matrix for supporting the active agent.

Both aspects are based on a concept of the invention, i.e. physically holding and retaining the composition in the passage formed by the capsule's walls until the blocking element in the capsule is dissolved upon exposure to liquid. The blocking element can be partly dissolved, such that the blocking element loses footing and is moved outside the capsule and through the outlet together with the liquid stream. According to some embodiments of the invention, both aspects are combined such that a part of the composition is physically retained inside the structure of the blocking element, and a part of the composition is blocked in the passage by the blocking element which forms a sealing element for the passage. Additionally, other parts of the oral delivery system can be formed of a dissolvable material, for example a plug sealing the inlet of the capsule's passage. This inlet is opened upon immersing the inlet of the passage into a liquid solvent. In order to avoid the composition to be released towards the inlet of the passage, a non-dissolvable retainer can be arranged in the capsule's passage between composition and an inlet opening of the passage. In general, however, elements other than the dissolvable blocking element of the passage are non-dissolvable in aqueous solutions, for example the lateral walls of the passage. In this context, non-dissolvable means that material and wall thickness provide structural integrity of the capsule for a duration which is substantially longer than the structural integrity of the blocking element when capsule and blocking element are immersed in water.

The above mentioned aspects of the invention can be implemented by the following geometrical relationships related to the arrangement of the composition in a composition section of the passage relative to the blocking element. The composition section can extend from a first end of the composition section, which is proximal to the outlet of the capsule's passage, to a second end of the composition section, which is distal to the outlet of the passage. The first end of the blocking element, i.e. the end proximal to the capsule's outlet, lies between the composition section and the outlet or abuts the end of the composition section, which is proximal to the outlet. The second end of the blocking element, i.e. the end distal to the capsule's outlet, lies at or between the first end of the blocking element within the capsule and the second end of the composition section or an inlet of the passage. In other words, the closest part or section of the blocking element is closer to the capsule's outlet than the section or part of the active agent, which is closest to the outlet. In this way, all composition located in the passage is controlled by the blocking element in both cases, i.e. when the blocking element is separated from the composition or when at least a part of the composition is within at least a part of the blocking element. Thus, this geometrical definition relates to both, the first and the second aspect of the arrangement of the blocking element and the composition within the capsule as defined above.

In a preferred embodiment, the capsule comprises a retainer arranged in the passage between the composition and the inlet of the passage. This ensures that all of the composition is delivered through the outlet of the capsule's passage and does not leave the passage through the capsule's inlet. The retainer can be provided as a grid filter, porous material or any liquid permeable plug, which allows a flow of liquid and forms a support of the active agent. The retainer does not lose structural integrity if a part of the blocking element is dissolved due to immersion of the capsule in liquid. Any openings in the retainer are preferably smaller than the smallest particle of the composition, i.e. the active agent. This also applies for the dissolvable blocking element and any openings of the blocking element of the capsule. In particular, the blocking element and the retainer can have the same general properties and dimensions. However, while the blocking element is dissolvable in aqueous compositions, the retainer does in general not significantly dissolve during the typical use of the delivery system of the invention. Alternatively, the retainer can also be of a dissolvable material, preferably having a structure and properties providing the same reaction on liquid like water as the blocking element. In one embodiment, the time for dissolving the retaining element in water is equal to or greater than the time for dissolving the blocking element upon immersion of contact into water.

In one embodiment, the retainer does not significantly impair the flow through the capsule's passage. Thus the retainer has preferably relatively wide openings or channels or pores. Consequently, the composition is formed of particles with a relative large particle size to avoid any transport of composition through the retainer. Thus, the size of the pores of the retainer and the blocking element can vary depending on the particle size of the pharmaceutical composition to be delivered. Alternatively or in combination therewith, the retainer can be arranged in an expanded or wider section of the passage within the capsule such that any impairments to the flow caused by the retainer are at least partly compensated by a larger cross section of the passage. Further, the same mechanisms can be used to enhance the flow through the blocking element, i.e. to expand the cross section at the section of the passage, at which the blocking element is arranged inside the capsule. The inlet can be provided with a cross section area equal to or greater than the cross section area of the outlet, both being smaller than the cross section area at the section between both ends at which the cross section is substantially constant.

In another embodiment, the retainer and/or the dissolvable blocking element are formed of elastic material, in particular elastic in a radial direction.

In a further embodiment, the blocking element and/or the retainer are in contact with an inner surface of the capsule (delimiting the passage in radial direction) by a press-fit. The blocking element, the retainer or both are elastic for providing the press-fit. Alternatively or in combination therewith, the wall forming the passage is elastic for providing a press-fit. Thus, the blocking element the retainer or both are (slightly) compressed in order to be fixedly positioned in the capsule by static friction. The outer surface of the blocking element, of the retainer or of both contacts the inner surface of the capsule's wall. The outer surface is urged towards the wall (or vice versa) by spring tension provided by the elastic properties of the blocking element, the retainer, the capsule's wall or any combination thereof. The capsule's wall extends from the inner surface to the outer surface of the wall; the thickness defining this extension of the wall is substantially constant and preferably less than 2 mm, less than 1 mm, less than 0.75 mm, less than 0.5 mm, less than 0.25 mm or less than 0.1 mm.

Preferably, the capsules have proportions of commonly used, pharmaceutical capsules. This enables the use of packaging equipment (stuffing, filling, packaging in a blister pack), which is already present and available for the preparation of known pharmaceutical capsules. In particular, capsules with standard sizes can be used, for example with a volume of 0.5-1.5 ml, in particular of 0.68 ml, 0.78 ml, 0.91 ml, 1.02 or 1.37 ml.

As preferred capsules, capsules with a diameter (at the capsule's center) in a range of 6 mm-10 mm, more preferably in the range of 7 mm-8 mm are used. Particularly preferred embodiments have outer diameters of about 7.6 mm, 7.5 mm, 7.4 mm or 7.3 mm. As an example, the capsule is a two-part capsule, one part of which has an outer diameter of ca. 7.3 mm (or of 7.34 mm), and the other part has an outer diameter of ca. 7.6 mm (or of 7.64 mm) at a tolerance of ±0.06 mm. The capsule is provided by introducing a connecting part of the capsule part with the smaller diameter into a connecting part of the capsule part with the more expanded diameter.

Further, as preferred capsules, capsules as a starting product for providing the inventive capsule, i.e. before removing parts of the closed ends (e.g. by cutting), with a lengths in a range of 20 mm-27 mm and more preferably in the range of 21 mm and 22 mm are used. Particularly preferred embodiments have length of about 26.6 mm, 25.3 mm, 24.2 mm, 23.3 mm, 23.1 mm, or 21.7 mm. As an example, the capsule is a two-part capsule, and has a length (if both parts are connected together) of ca. 21.7 mm (or of 7.34 mm). In a similar example, the capsule is a two-part capsule, one part of which (e.g. the part with the smaller diameter) has a length of about 18 mm (e.g. about 18.4 mm) and the other part (e.g. the part with the more expanded diameter) has a length of about 10 mm (e.g. about 10.72 mm).

Preferably, the capsule according to the invention has a ratio of length to diameter of less than 8, less than 6, less than 5 or less than 4. This provides a sufficient flow through the capsule when unloading (i.e. administering) the capsule. The ratio is preferably in the range of 2.5-3.2, more preferably between 2.5 and 3 and particularly preferred about 2.8 or 2.84. As an advantage, commonly used capsules and commonly used and readily available devices for their preparation, handling and manufacturing can be used, since this ratio corresponds to standard sizes of capsules, which readily available.

The preferred capsules used as starting product for realizing the invention have hemispherical ends. For providing the invention according to a first aspect of the invention, outer parts of these ends are removed (e.g. cut off, punched or drilled). In this way, the openings (inlet and outlet) are provided. The generated openings have a cross section smaller than the cross section of the capsule which leaves shoulders as supports for the blocking element and/or the retaining element. The preparation of the capsules, i.e. of the two-part capsules, by removing parts of both ends is carried out before introduction of the blocking element, the retaining element and/or the composition. Preferably, the capsules are prepared by preparing (i.e. removing the respective ends) of both individual capsule parts before the parts are connected together forming one capsule according to the invention.

The capsule according to the invention is preferably provided in two parts, e.g. in form of a body and a cap. The outer cross section of the body is about the inner cross section of the cap or is smaller than the inner cross section of the cap. The proportions of the capsule are suited for introducing (at least) a part of the body (the connection part) into (at least) a part of the cap.

If two-part capsules are used, both parts can be connected by any suitable connection, even by connection elements not suited for swallowing by a patient, since the use of the inventive capsule usually does not comprise to digest the capsule. Embodiments of the connection comprise: a press fit between a part of the thinner capsule part and the part of the thicker capsule part in which the part of the thinner capsule part extends; an adhesive connection between the part of the thinner capsule part and the part of the thicker capsule part in which the part of the thinner capsule part extends, wherein the glue connection can be combined with the press fit or not; and an outer ring connecting both parts by press-fit and/or by an adhesive connection. Such an outer ring can be provided by a banderole, e.g. a banderole having an adhesive surface lying on both parts. If an outer ring is used, the ring overlaps both parts. If an outer ring is used, the outer ring or sleeve can gap a short distance between the capsule parts, can connect both parts as abutting parts, or can fix both parts partly overlapping each other.

According to a further aspect of the invention, similar capsules are used as described above, however, with a distinct modification to provide the inventive capsule starting from known pharmaceutical capsules or other capsules. According to this aspect of the invention, at least one of the openings is provided by cutting a closed end of a capsule part starting from the apex of the closed end along the longitudinal axis of the capsule (part). Preferably, the cuts extend according edges of a spherical triangle. The apex of the capsule or capsule part is an intersection of two circular arcs of the spherical triangle. The cuts are along a solid angle of about 90°. The arcs start from the apex of the closed end of the apex and end at the beginning of a cylindrical part of the capsule. Preferably, all arcs (i.e. slits or cuts) are equally distributed in a cross section perpendicular to the longitudinal axis of capsule. Preferably, are equally distributed with a difference angle of 360°/n in a plane perpendicular to the longitudinal axis of the capsule. According to an embodiment of the invention, n is 3, 4, 5, 6, 7, 8, 9, 10 or more than 10. A particular preferred embodiment provides n=4, separating the hemisphere of the close ends of the capsule into four spherical triangle, each of 90° in azimuthal direction and 90° in radial direction referring to the longitudinal axis of the capsule. By these slits, the capsule end is modified on to a controllable blocking element in form of a one-way valve. Preferably, only the outlet end of the inventive capsule is provided as one-way valve, while the inlet end if provided with a retainer element.

Alternatively or in combination therewith, the passage and/or a conduit forming the passage comprises support elements for supporting the blocking element and/or the retainer in the passage during storage. This can be provided by additional support elements (preferably non-dissolvable) formed by the tapered walls of the capsule at the outlet (or the inlet). Thus, the elements can be integrally formed with the capsule's walls delimiting the passage. The blocking element, the retainer or both can be supported in the correct position in the passage by shoulders formed by the capsule's walls in the passage by an abrupt extension of the cross section area of the inner passage of the capsule along the passage itself in form of shoulders of a part of the capsule. Alternatively, an elevation extending into the passage can be used to define a support element. Further, complimentary forms can be used, for example a section of the conduit, which has a reduced cross section or, in other words a tapered section of the conduit. Supporting elements (e.g. stoppers or shoulders) integrally formed with the passage comprise a surface or a form complementary to a surface or a form of the blocking element and/or the retainer for at least partly engaging with the blocking element and the retainer, respectively. Alternatively or in combination therewith, additional support elements can be used, for example at least one rod at least partly extending from the inner capsule wall into the passage in a radial direction or a grid or a filter extending radially into the capsule's passage in order to engage or contact the blocking element and/or the retainer.

The inventive capsule comprises a middle section with a substantially constant cross section as well as two tapered sections at both ends. Both tapered sections comprise an opening, both openings being opposed to each other and being preferably perpendicular to a longitudinal axis of the capsule. The openings are defined by circles which lie within planes perpendicular to the longitudinal axis of the capsule. The capsule is preferably formed of two parts which are connected to each other by plugging, further, the capsule can also be integrally formed in principle. The capsule comprises the inlet, the outlet as well as inner surface, which is partly used to hold back a composition in redial direction. The capsule further comprises a retainer located at the inlet and, a dissolvable blocking element, which is located at the outlet end of the capsule as well as a pharmaceutical composition as particles which are enclosed between a part of the inner surface of the capsule, the blocking element and the retaining element. Since the retainer and the blocking element is permeable for liquid, a passage is formed between the inlet and the outlet through the retainer, the composition and the dissolvable blocking element. Upon applying a vacuum at the outlet, a liquid located at the inlet and outside the capsule will enter the inlet, flow through the retainer as well as through the composition and will reach the blocking element. Then, the blocking element will be dissolved (completely or partly) and the composition flows, together with the liquid as well as parts of the dissolved blocking element, to the outlet towards the patient's mouth. The part of the capsule comprising the outlets comprises an outer diameter which equals or is slightly greater than the inner diameter of the capsule's part comprising the inlet within the middle section of the capsule, such that the inlet part can be pushed onto the outlet part providing a mechanical connection. In one embodiment, the connection is provided by a snap connection provided by a circumferential grove or elevation towards the longitudinal axis of the capsule or towards the opposite direction, such that two complimentary connection elements are formed, each of the capsule parts comprising one of these elements, which engage when the capsule parts are put together forming a locked mechanical connection.

In a embodiment having a simple construction, the passage of the oral delivery system is formed of a capsule enclosing the composition to be delivered, the blocking element and the retainer, the capsule being formed of two parts having the shape and dimensions of known capsules used for pharmacological formulations. Therefore, large parts of the manufacturing process can be reused for producing the oral delivery system according to the invention. According to this embodiment, one part of the capsule is provided as outlet part, and the second part of the capsule is an inlet part, preferably comprising a retainer in form of a filter or a grid formed of non-dissolvable material. The blocking element is arranged or fitted into the capsule's passage, e.g. into the outlet part, the inlet part, or both, and separates the outlet of the capsule from the composition provided in the passage in order to retain the composition until at least a part of the blocking element is dissolved. The blocking element is preferably completely or at least partly arranged in the outlet part of the capsule. The outlet of the capsule is formed at an end of a part, preferably at an outer end of the outlet part. In the same way, the inlet is formed at an end opposed to the outlet of the capsule. Thus, the capsule provides a passage leading from the inlet, through the retainer (filter or a grid), through active agent, through the blocking element as well as through an outlet of the capsule. An additional mouthpiece and/or extension conduit could be connected to the capsule, preferably to the outlet part. Thus, the capsule preferably provides a connection section adapted for being (releasably) connected to the additional mouthpiece or extension conduit. The connection between two parts forming the capsule is preferably more stable than the connection between additional mouthpiece and connection section of the capsule. In this way, the parts forming the capsule are not separated, if the capsule is pulled from the additional mouthpiece.

The composition is preferably provided as particles with a minimum particle size, for example pellets, located between the blocking element and the retainer, i.e. the inlet of the capsule.

Advantageously, the inlet part of the capsule has a cross section larger than the inner cross section of a straw (or another extension conduit or additional mouthpiece) in order to allow to arrange or attach the outlet part and the outlet of the capsule into the straw and, at the same time, to ensure that the inlet part of the capsule can not enter the straw. Thus, the outer cross section of the outlet part of the capsule differs from (is smaller than) the input part of the capsule and, at the interface between inlet part and outlet part, a shoulder is formed adapted to engage with an end of an end of a straw or an additional mouthpiece or extension conduit. In an example, the straw forming the additional mouthpiece has an inner diameter or ca. 5 mm, 6 mm, 7 mm, 8 mm, 9 mm or 10 mm±30% or ±20%. Accordingly, the capsule or the part of the capsule for introduction of the mouthpiece has an outer diameter equal to the inner diameter of the mouthpiece, in addition of a small additional outer diameter equal to about 1%, 2%, 3%, 5% or 10% of the outer diameter. This ensures an adequate (releasable) press fit between straw and capsule. At least one of the straw's or the capsule's material provides elastic properties. In stead of or in addition to slightly differing diameters, the cross section area or the cross section form of the (inner) mouthpiece or straw can slightly differ from the cross section area or the cross section form of the (outer) capsule in order to provide a mechanically stable connection between capsule and straw. The connection between straw and capsule prevents the capsule from falling out of the straw, and, at the same time, provides a liquid connection between straw and passage (or outlet) provided by the capsule.

As the straw, additional mouthpiece or extension conduit, a tube having a grip section with or without elevated gripping elements can be used. Any conventional straw could be used into which the outlet part of the capsule can be inserted. Preferably, the outlet part of the capsule can be inserted without force or with marginal force (<10 N, <5 N, <2 N, <1 N, <0.5 N or <0.1 N), connecting the capsule to the straw by press-fit. The force necessary to remove the capsule from the straw is lower than the force necessary to separate one part of the capsule from another. The invention can be realized by an oral delivery system formed of a capsule adapted to be at least partly fitted into an additional mouthpiece or a straw or another extension conduit, or can be realized by a combination comprising the capsule as well as instructions for use of the capsule setting out that the capsule can be plugged onto a straw. In a particular embodiment, the combination comprises a straw into which the outlet part (but not the inlet part) of the capsule can be plugged in. In general, the capsule providing the passage and containing the active agent provides a surface or an attachment member for engaging this part into a connectable, dedicated extension conduit, which comprises a complementary connection element with a shape complementary to the outlet section of the capsule. In this way, the passage of the capsule containing the composition can be sealingly connected to each other and form one common (elongated) passage.

In one embodiment, the inlet part if the capsule has a shape, which prohibits the insertion of the inlet part into a potential mouthpiece or into the complementary connection element. Thus, the inlet part is not complementary to the complementary connection element of a connectable mouthpiece. The inlet part can have an outer diameter significantly larger than the inner diameter of a connectable complementary connection element, i.e. an end of a straw, or can have a larger cross section than the inner diameter of the straw's end, i.e. complementary connection element. Additionally or in combination therewith the form of the capsule's complementary connection element can be incompatible to the inlet part, e.g. by having a projection. In this way, only the outlet part can be fitted into a mouthpiece, straw or into the complementary connection element, and the inlet part can not be connected to the mouthpiece. In a preferred embodiment, the inlet part has a colour different to the colour of the outlet part. In this way, in particular if provided as capsule, the inlet part can be distinguished from the outlet part, enabling the use in one direction and preventing the use in the "wrong" direction, together with a straw.

The concept underlying the invention is further realized by a method for releasable sealing a capsule, comprising: filling a composition into a capsule, the capsule forming a passage, and occluding the passage with a dissolvable blocking element as described above. The passage formed by capsule is enabled by opening two opposed ends of a capsule, e.g. by cutting, by providing a capsule or two parts of a capsule with opening at the respective ends or by opening the ends of two parts, together forming a capsule. The composition can be delivered to a patient by drawing liquid into the capsule's passage, dissolving the blocking element in the capsule using the liquid transported into the passage, the dissolving step enabling the composition to be transported and applied to the patient. As mentioned above, the blocking element can be dissolved by drawing liquid into the straw and by immersing a part of the capsule into liquid before drawing liquid through the passage of the capsule.

In order to allow liquid to be drawn or transported into the capsule's passage for dissolving the blocking element within the capsule, the blocking element, any supporting elements, as well as any retainers in the passage are preferably permeable for gas and/or for liquid. In this way, liquid or gas can be easily transported along the passage. In order to direct the flow, the walls of the capsule forming the passage are continuous and impervious. In the same way, the blocking element as well as walls of the capsule physically delimit the composition. The composition is formed of solid particles, the solid particles having a minimum particle size, to which the micro-structure size channels, pores or density of the blocking element corresponds. Preferably, the minimum particle size is 0.1 mm, 0.2 mm, 0.5 mm, 1 mm, 2 mm, 3 mm, 4 mm or 5 mm, and the corresponding (maximum) pore or microstructure size of the blocking element is at least slightly smaller and is at most ca. 90%, 80%, 70%, 50%, 30%, 20% or 10% of the minimum or average particle size of the active agent. Thus, the blocking element is preferably formed of a fibrous web or mesh, for example a filament fabric of a dissolvable material. Since the dissolving rate or dissolving speed depends on the structure size, preferably very small filaments are used, for example a liquefied solid which has been pressed through a thin nozzle before it is solidified, e.g. by cooling. Thin filaments or webs manufactured in this way are provided in a structure with a high ratio of surface area vs. volume. Due to this high ratio and the choice of a suitable material, the blocking element can be dissolved in a short time period. Instead or in combination with a mesh or fibrous web, fabric or textile of a dissolvable material, materials with porous structures could be used, for example porous solid, membranes, which are permeable for gas and/or liquid or even a solid continuous block with at least one passage or longitudinal channel. Firstly, the material forming the blocking element is such that a high dissolution rate in aqueous compositions is provided and allows pressure compensation in the course of immersing the oral delivery system into liquid or drawing liquid into the passage. The term "high dissolution rate" means a dissolution rate significantly higher than the rate of the material of all other elements, e.g. significantly higher than the rate of gelatin of gelatin capsules forming the capsule.

Throughout the description and the claims, the term "dissolvable" does not relate to solubility in the sense of the amount of a substance, which can be dissolved in total. Rather, "dissolvable" relates to the rate in which the blocking element (or other dissolvable elements) physically changes when brought into contact with a solvent (in general water). The physical change is a loss of structural integrity. The physical change is caused by dissolving at least a part of the dissolvable element (e.g. the blocking element) and results in a structural change such that at least a part of the composition is released. On one hand, "dissolvable" can imply that only a very small amount of the blocking element can be dissolved in a short time period, if it is given that this causes a substantial structural change resulting in the removal of the blocking element, such that the remaining blocking element is carried away from the passage by the liquid flow. On the other hand, the "dissolvable" can imply that only a high percentage or all of the blocking element is dissolved in a short time period such that the blocking element reaches the patient's mouth as a solution. Again, "dissolvable" is a measure for the time needed until the blocking element (or any other dissolvable element) releases a substantial part or all of the composition. Thus, the property "dissolvable" depends on chemical properties of the used substance and on physical properties like surface area, structure, pore size, flow resistance, adhesive force or friction force between blocking element and side walls of the passage, and other. In the same way, "non-dissolvable" throughout the claims and the description denotes the property of the respective element (e.g. the capsule and the capsule's wall) to direct fluid or fluid flow and to hold other elements for a certain duration, which is substantially larger than the duration associated the release of the composition. Thus, non-dissolvable also depends on physical and chemical properties as discussed above with regard to "dissolvable". Dissolvable and non-dissolvable can relate to corresponding, similar or identical materials if their respective structure provides a short time for dissolving dissolvable elements (thereby releasing the composition) as well as a long time for dissolving non-dissolvable elements like the walls of the capsule, or other. For example, the time needed between the first contact of a dissolvable element (e.g. the blocking element) and the release of a substantial amount (or all) of the composition can be in the range of 0.1-100 sec, preferably, 0.5-10 sec or 1 sec-3 sec. For a non-dissolvable element, e.g. one or both parts of the capsule and the retainer, the time needed between the first contact with the same solvent, e.g. water, should be >5 min, >1 h, or >1 d order to avoid any structural degradation before disposal of the capsule or before the capsule has been dried again by environmental air.

The density, mesh size or pore size of the blocking element is not necessarily constant along the longitudinal axis of the passage. Rather, a longitudinal section with a dense mesh or pore size of the blocking element can be used to confine the active agent, and another section attached thereto or formed therewith can be used to mechanically stabilize the first section. Further, the mesh size, pore size or density can increase or decrease in a radial direction towards the center of the passage. In case of variable pore size, mesh size or density along the longitudinal axis of the capsule's passage, the particle size of the active agent, i.e. the respective minimum particle size, is adapted to the minimum mesh size, pore size or density of the blocking element. In the case of radially variable pore size, mesh size or density of the blocking element, the particle size of the composition is adapted to the maximum pore size, mesh size or density of the blocking element.

The blocking element can be formed of a combination of the structures disclosed above, for example can be formed of a fibrous web in combination with a membrane, the membrane having holes for pressure compensation. The membrane can have pores, holes or small channels to enable pressure compensation and to be gas and/or liquid permeable.

Further, the blocking element can be provided as a film (preferably with pores), a membrane (preferably with pores), a sieve, a grid or a plate (preferably with pores) comprising dissolvable material. Further, the blocking element can be provided as a combination thereof, e.g. formed as stack.

The dissolving properties of the material forming the blocking element are preferably adapted to the liquid to be drawn into the passage. Any pharmaceutical acceptable liquid can be used in the context of the present invention, i.e. any liquid which can be used in pharmaceutical compositions or nutrition, in particular water, water based drinks or aqueous solutions or other pharmaceutically acceptable liquids substantially being based on water. Thus, the blocking element is preferably dissolvable in a liquid like water, water based drinks or aqueous solutions or other pharmaceutically acceptable liquids substantially being based on water. Preferably, the liquid comprises sweeteners and/or flavouring agents.

The aqueous solution can also comprise other compounds such as salts or buffers, preferably compounds which are frequently used in pharmaceutical compositions, such as pharmaceutical acceptable salts.

According to the present invention, the blocking element comprises a material which is pharmaceutical acceptable and which is essentially dissolvable in liquid, e.g. aqueous compositions, in particular water, juice, tea or other beverages. The material in essentially dissolvable in liquid to be drawn into the capsule under the conditions applied, i.e. at ambient temperature and ambient pressure. According to a preferred embodiment, the blocking element consists essentially of a material which is pharmaceutical acceptable and which is quickly dissolvable in the liquid to be drawn in the passage under the conditions applied. In this context, "essentially dissolvable" refers to the blocking element or parts thereof end refers to the destruction, i.e. substantial structural degradation of the blocking structure of the blocking element. Thus, the blocking element is adapted to be at least partly dissolvable such that the blocking element reduces or loses mechanical contact to the wall defining the passage in order to be movable relative to the wall. The blocking element can comprise dissolvable material as well as dissolvable material, wherein the dissolvable material at least partly dissolves upon contact with the solvent causing a significant reduction of mechanical connection between blocking element and wall and/or among areas or parts of the blocking element itself. This significant reduction of mechanical connection leads to a movement of the blocking element relative to the wall/inner surface of the capsule, in particular at the outlet of the capsule, and, finally, to the disappearance of the blocking element from the capsule and the passage.

In a particular preferred embodiment, the dissolvable material may comprise a water-dissolvable thermoplastic material, i.e. a material which can be melted, and formed as a melt, (preferably pharmaceutically acceptable) formed by injection moulding, in particular as thin fibers, filaments or as foam or foam films comprising pores, perforations or a combination thereof. In particular, modified starch, sugars (e.g. as candy floss or cotton candy or as a permeable pressed block of sugar particles), caramel, or blends thereof can be used as thermoplastics. The thermoplastics can be melted and spun as thin filaments or formed by mould injection as a plate or membrane with pores, through holes perforations or a combination thereof. For example, the same materials can be used which are used to manufacture bio-degradable food packages or food compliant foils. In this context, thermoplastic materials comprise thermoplastic polymers as well as other, preferably pharmaceutically acceptable, materials (e.g. sugar, starch or derivates thereof) which can be processed as described above. According to the invention, the dissolvable material forms the structure of the blocking element as mechanically stabilizing element.

In particular, the blocking element comprises a water dissolvable compound, preferably a water dissolvable polymer or mixtures of two or more of these compounds. The blocking element may for example comprise polyethylene glycol, polylactic acid, hydrolysed gelatine, mannite or water dissolvable cellulose, such as hydroxypropylmethyl cellulose and hydroxypropyl cellulose, or a mixture of two or more thereof. Furthermore, the blocking element may comprise: sugars, such as saccharide, lactose, fructose, polylactide, starch, modified starch, starch derivatives, cellophane or any blends thereof. Preferably, the blocking element consists essentially of one or more of theses compounds.

According to the present invention, the blocking element may comprise further compounds which may also be non-dissolvable in the liquid to be drawn into the passage as long as the blocking element as such allows the release of the composition by structural degradation, i.e. a pharmaceutical composition comprising an active agent upon contact with liquid which is drawn into the passage, for example it may comprise diluents, sweeteners, flavouring agents, or colouring agents.

The passage, the capsule's wall defining the passage by the capsule's inner surface and the retainer and other non-dissolvable elements extending in the passage can be formed of any suitable materials having a structure that does not degrade until these elements are dried again after use in standard conditions (air, 1013 hPa, 20° C., rel. humidity <95% or <80%). Such materials comprise paper, plastic such as propylenelstyrene copolymers, polyproylene, high density polyethylene, low density polyethylene and the like. In this regard, the term non-dissolvable is defined as given above.

In general, all materials for providing the capsule can be used, which are used for manufacturing readily available, pharmaceutical capsules. This allows to provide the inventive capsule without complex changes to the manufacturing process already used for standard pharmaceutical capsules.

However, since the capsule according to the invention is not (necessarily) digested when administering the capsule, a broad range of other materials can be used. These material for providing the capsule (i.e. the capsule's wall) comprise natural and synthetic polymers, impervious fabrics (like paper or textile, for example impregnated, e.g. with a thermoplast, wax, oil or similar, or coated with a impervious coating) and similar materials providing an impervious capsule. These materials also comprise moulded or cast materials like plastics, e.g. polyphines like polyethene or polypropene or co-polymers thereof, polystyrole, polyvinylchloride, polyacrylnitrile, polyamide, polyester, LD-PE, LD-PP, HD-PE, HD-PP, materials like nitrile NBR (nitril butadien rubber), isobutylene-isoprene-rubber, styrene-butadiene, styrene-butadiene co-polymers, polyurethane, polyacrylate, polyisoprene (natural or synthetic), choloprene, silicone, fluorosilicone, fluorocarbon, ethylene propylene co-polymers, epichlorohydrin, hydrogenated nitrile, or any mixtures or polymer blends thereof. Since the capsule according to the invention (in contrast to common pharmaceutical capsules) is used for packaging only and does have to be biocompatible, any materials used for packaging (e.g. for manufacturing blister packages) can be used. Further, the standards for these materials are lower than for capsules, which are swallowed. This allows a high flexibility as regards the selection of the material.

Further, the wall thickness can be provided in a range broader than the allowable range used within commonly used pharmaceutical capsules since the wall does not have to be opened by digestion within the inner digestive tract. Thus, thicker walls can be used providing a higher stability, e.g. in the range of 0.1-2 mm, 0.4-1 mm or even more than 2 mm. If the controllable blocking element is provided in form of a one-way valve, the wall thickness at the capsule's end(s), at which the on-way valve is provided by the capsule's wall a slits separating sections of the capsule's wall, the wall is preferably thin. Since the one-way valve is provided by movable parts of the capsule's wall, in particular the parts of the capsule which provides the one-way valve have a low thickness. Further, these parts are preferably formed of flexible material. The mechanical properties (the elastic properties) of the capsule's wall (defined by the material and the dimensions, in particular the wall thickness) are preferably suited to allow a substantial flow of liquid (and composition), if a patient applies a vacuum to an opening of the capsule (in particular to the one-way valve) for administering the composition by drawing the liquid through the capsule. Thus, if a one-way valve is used, the structure and the material of the capsule at the end of the capsule providing the valve or of the complete capsule provide a flexibility allowing an easy access to the composition within the capsule by drawing liquid (a drink) through the capsule. Parts or sections of the capsule not providing the one-way valve can be provided by the capsule itself (having a high flexibility) and a support, e.g. in form of a sleeve or a ring extending around the capsule for increasing the stiffness of the capsule at these sections of the capsule. The sleeve or ring is provided by a material having an elasticity, which is substantially lower than the elasticity of the capsule parts (e.g. one end of the capsule) providing the one-way valve.

Preferably, the composition comprises an active substance, which includes foods, food supplements, nutrients, active pharmaceutical ingredients, vitamins, and other beneficial agents, in particular the composition to be orally delivered is a pharmaceutical composition comprising an active pharmaceutical ingredient. As used herein, the active pharmaceutical ingredient can include any physiologically or pharmacologically active substance that produces a localized or systemic effect in a patient. The term active pharmaceutical ingredients includes antibiotics, antiviral agents, anepileptics, analgesics, anti-inflammatory agents and bronchodilators, and may be inorganic and organic compounds, including, without limitation, drugs which act on the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autacoid systems, the alimentary and excretory systems, the histamine system and the central nervous system. Suitable agents comprised by the substance may be selected from, for example, polysaccharides, steroids, hypnotics and sedatives, psychic energizers, tranquilizers, anticonvulsants, muscle relaxants, antiparkinson agents, analgesics, anti-inflammatories, muscle contractants, antimicrobials, antimalarials, hormonal agents including contraceptives, sympathomimetics, polypeptides and proteins capable of eliciting physiological effects, diuretics, lipid regulating agents, antiandrogenic agents, antiparasitics, neoplastics, antineoplastics, hypoglycemics, nutritional agents and supplements, growth supplements, fats, ophthalmics, antienteritis agents, electrolytes and diagnostic agents.

Examples of specific active pharmaceutical ingredients comprised by the pharmaceutical composition and useful in this invention include prochlorperazine edisylate, ferrous sulfate, aminocaproic acid, mecamylamine hydrochloride, procainamide hydrochloride, amphetamine sulfate, methamphetamine hydrochloride, benzphetamine hydrochloride, isoproterenol sulfate, phenmetrazine hydrochloride, bethanechol chloride, methacholine chloride, pilocarpine hydrochloride, atropine sulfate, scopolamine bromide, isopropamide iodide, tridihexethyl chloride, phenformin hydrochloride, methylphenidate hydrochloride, theophylline cholinate, cephalexin hydrochloride, diphenidol, meclizine hydrochloride, prochlorperazine maleate, phenoxybenzamine, thiethylperazine maleate, anisindione, diphenadione erythrityl tetranitrate, digoxin, isoflurophate, acetazolamide, methazolamide, bendroflumethiazide, chlorpropamide, tolazamide, chlormadinone acetate, phenaglycodol, allopurinol, aluminum aspirin, methotrexate, acetyl sulfisoxazole, hydrocortisone, hydrocorticosterone acetate, cortisone acetate, dexamethasone and its derivatives such as betamethasone, triamcinolone, methyltestosterone, 17b-estradiol, ethinyl estradiol, ethinyl estradiol 3-methyl ether, prednisolone, 17-b-hydroxyprogesterone acetate, 19-nor-progesterone, norgestrel, norethindrone, norethisterone, norethiederone, progesterone, norgesterone, norethynodrel, aspirin, acetaminophen, indomethacin, naproxen, fenoprofen, sulindac, indoprofen, nitroglycerin, isosorbide dinitrate, propranolol, timolol, atenolol, alprenolol, cimetidine, clonidine, imipramine, levodopa, chlorpromazine, methyldopa, dihydroxyphenylalanine, calcium gluconate, ketoprofen, ibuprofen, cephalexin, erythromycin, haloperidol, zomepirac, ferrous lactate, vincamine, phenoxybenzamine, diltiazem, milrinone, captropril, mandol, quanbenz, hydrochlorothiazide, ranitidine, flurbiprofen, fenbufen, fluprofen, tolmetin, alclofenac, mefenamic, flufenamic, difuninal, nimodipine, nitrendipine, nisoldipine, nicardipine, felodipine, lidoflazine, tiapamil, gallopamil, amlodipine, mioflazine, lisinopril, enalapril, captopril, ramipril, enalaprilat, famotidine, nizatidine, sucralfate, etintidine, tetratolol, minoxidil, chlordiazepoxide, diazepam, amitriptyline, and imipramine. Further examples of the substance comprise proteins and peptides which include, but are not limited to, insulin, colchicine, glucagon, thyroid stimulating hormone, parathyroid and pituitary hormones, calcitonin, renin, prolactin, corticotrophin, thyrotropic hormone, follicle stimulating hormone, chorionic gonadotropin, gonadotropin releasing hormone, bovine somatotropin, porcine somatropin, oxytocin, vasopressin, prolactin, somatostatin, lypressin, pancreozymin and luteinizing hormone.

The composition to be delivered, and in particular the pharmaceutical composition, is preferably in the form of small pellets, preferably having a mean pellet size of between 20 µm and 1000 µm, more preferably of between 50 µm and 800 µm, in particular between 100 µm and 500 µm. Such small pellets, which can be described as free-flowing spherical particulates, are typically produced by the agglomeration of fine powders or granules of, for example, active pharmaceutical ingredients and excipients using appropriate processing equipment. Various methods for the production of pellets of a desired size are known to the person skilled in the art, for example pellet production by layering techniques, such as solution layering, suspension layering and powder layering, by extrusion techniques or by granulation techniques.

The invention further comprises a combination of (a) a capsule or a plurality of capsules and (b) a mouthpiece or extension conduit. Preferably, this combination further comprises a packaging, e.g. a blister package, in which capsule (s) and extension conduit are arranged. The extension conduit can be provided by a straw with a length of for example 3 cm-20 cm and a diameter in the range of 4 mm-15 mm, preferably with a diameter of about 6-9 mm or 7-8 mm. The inner diameter of the straw is slightly smaller than the outer diameter of the capsule, in particular of the end of the capsule comprising the outlet. The extension conduit, in particular a capsule receiving end of the capsule is suited and arranged to receive at least a part of the capsule (preferably the end of the capsule comprising the outlet) and to provide a press fit with the capsule, in particular with the end of the capsule comprising the outlet. Advantageously, the capsule is provided in a standard size of a pharmaceutical capsule and the size of the mouthpiece, in particular the inner diameter, is selected to receive and to (tightly) hold the capsule. The combination can further comprise information and direction for use describing the steps of plugging the capsule into the mouthpiece, immersing the capsule (fit into the moughpiece) into a drink and to draw the drink through the capsule into the mouth. In addition the combination can further comprise an outer packaging in which all components of the combination are arranged.

According to a first aspect, the invention relates also to the following items:

1. Capsule suitable for releasably storing a composition to be administered, the capsule defining a passage (108, 208), in which a dissolvable blocking element (120, 220) and a composition to be administered (130, 230) are arranged, the blocking element (120, 220) being fluid permeable and, in an non-dissolved condition, the blocking element (120, 220) being arranged in the passage (108, 208) defined by the capsule to releasably block delivery of the composition (130, 230) to an outlet (110, 210) of the passage (108, 208) at an end of the passage.

2. Capsule of item 1, wherein the blocking element (120, 220) and the composition (130, 230) is arranged at least partly coextensive and/or the blocking element (120, 220) is arranged between at least parts of the composition (130, 230) and the outlet (110, 210) and/or the blocking element (120, 220) is arranged to separate the composition (130, 230) from the outlet (110, 210).

3. Capsule of item 1 or 2, wherein the composition (130, 230) is arranged in an composition section (231) of the passage (108, 208), the blocking element (120, 220) extending radially in the passage (108, 208) at a position between or including a first end of the composition section (231), the first end being proximate to the outlet (110, 210) of the passage (108, 208), and the outlet (110, 210).

4. Capsule of one of the preceding items, wherein the capsule defining the passage (108, 208) further comprises an inlet (150, 250) at another end of the passage opposed to the outlet (110, 210) as well as a fluid permeable, non-dissolvable retainer (140, 240), the retainer (140, 240) being arranged between the composition (130, 230) and the inlet (150, 250) of the capsule to block any flow of the composition (130, 230) through the retainer (140, 240) towards the inlet (150, 250).

5. Capsule of one of the preceding items, wherein the passage (108, 208) is formed by the inner surface of a wall forming the capsule, the capsule further comprising support elements for supporting the blocking element (120, 220) in the passage (108, 208), the support elements comprising: an inner surface of the wall, a section of the wall tapering towards the outlet, an expanded cross section of the conduit, non-dissolvable filters or rods radially extending form the inner surface of the wall as in the passage (108, 208), a shoulder or an elevation of the wall extending into the passage (108, 208) or a combination thereof.

6. Capsule of one of the preceding items, wherein the capsule (102) comprises an outlet part (102a) in which the blocking element (120, 220) is fitted into, and inlet part (102b) comprising a retainer (140, 240) attached to or fitted into the capsule in form of a filter and/or a grid formed of non-dissolvable material.

7. Capsule of one of the preceding items, wherein the inner surface of the capsule enclosing the composition (130, 230), except for the blocking element (120, 220), is formed of material being non-dissolvable in water, and wherein the blocking element (120, 220) is formed of water-dissolvable material.

8. Capsule of one of the preceding items, wherein the blocking element (120, 220) comprises at least one of fibrous web, fabric, textile, porous solid, gas and/or liquid permeable membrane and a solid block with at least one longitudinal pressure compensation channel.

9. Capsule of one of the preceding items, wherein the blocking element (120, 220) comprises polyethylene glycol, polylactic acid, water dissolvable cellulose, such as hydroxypropylmethyl cellulose, hydroxypropyl cellulose, hydrolysed gelatine or mannite or mixtures of two or more thereof 10. Capsule of one of the preceding items, wherein the composition (130, 230) is provided in the form of particles having a minimum particle size, the minimum particle size being provided to ensure the blocking of delivery of the composition (130, 230) to the outlet, the minimum particle size being larger than a pore size, a channel cross section, a channel diameter or a mesh size provided by the fluid permeable blocking element (120, 220).

11. Capsule of one of the preceding items, wherein the blocking element (120, 220) is comprised of a dissolvable material and provides structure, the combination of the material and the structure providing a dissolving rate of at least 30%, at least 50%, at least 60%, at least 70%, at least 80%, at least 90%, at least 95% or at least 99% of weight percent for a total immersion in water at 20° C. and 1013 hPa for a duration of at most 30 s, 20 s, 10, 5 s, 3 s or 2 s, wherein the dissolvable material is pharmaceutically acceptable.

12. Capsule of one of the preceding items, comprising an outlet outer wall section at the outlet, the outer wall section forming a complementary connection element adapted to engage with an extension conduit (104), the extension being adapted to be sealingly attached to the complementary connection element, to the outlet or to the passage (108, 208).

13. Package comprising a plurality of the capsules according to one of the preceding items, the package comprising a reclosable container containing the capsules or at least one blister package, the blister package defining individual storages each containing one capsule which can be retrieved from the individual storage by opening the individual storage.

14. Method for releasably sealing a capsule defining a passage comprising a composition to be orally administered, comprising the steps of:
    providing a capsule with an inlet and an outlet being connected by the passage (108, 208);
    occluding the passage (108, 208) with a blocking element (120, 220), the blocking element (120, 220) comprising dissolvable material and having a fluid permeable structure; and
    filling composition into the composition chamber.

15. Use of a capsule according to one of items 1-12 for the administration of a medicament or solid particles comprising a pharmaceutical preparation.

16. Use of a capsule according to one of items 1-12 for taste-masked administration of a composition to be administered.

17. Method for oral application of a composition to be orally administered, comprising the steps of:
    providing a capsule with an inlet and an outlet connected by a passage, the capsule being formed of non-dissolvable material, the passage comprising the composition as well as a dissolvable blocking element, the blocking element being arranged in the passage at the outlet to block delivery of the composition through the outlet of the passage;
    dissolving the blocking element;
    by dissolving the blocking element, opening a passage section between the composition and the outlet for the composition; and
    applying the composition to a patient through the outlet and the opened passage.

18. Method of item 17, wherein dissolving the blocking element comprises: immersing the dissolvable blocking element or the capsule's inlet into a solvent or applying a solvent to the blocking element by drawing fluid through the inlet and the blocking element and by compensating the low pressure resulting therefrom by supplying the solvent into the passage through the inlet of the capsule.

According to a second aspect, which can be freely combined with the preceding first aspect, the invention also comprises following items:

I. Capsule suitable for releasably storing a composition to be administered, the capsule defining a passage, in which the composition to be administered is arranged, wherein the capsule comprises a controllable blocking element in form of a dissolvable blocking element within the passage or in form of a one-way valve, wherein the dissolvable blocking element is fluid permeable and, in an non-dissolved condition, the dissolvable blocking element is arranged in the passage defined by the capsule to releasably block delivery of the composition to an outlet of the passage at an end of the passage, and wherein the one-way valve is part of the capsule and comprises at least one moveable lid obstructing an opening of the passage, the one-way valve providing a flow direction though the passage towards the outlet and blocking in the opposite flow direction.

II. Capsule of item I, wherein the dissolvable blocking element and the composition are arranged at least partly coextensive, and/or the controllable blocking element is arranged between at least parts of the composition and the outlet, and/or the controllable blocking element is arranged to separate the composition from the outlet or from an external area next to the outlet.

III. Capsule of item I or II, wherein the composition is arranged in an composition section of the passage, the dissolvable blocking element extending radially in the passage at a position between or including a first end of the composition section, the first end being proximate to the outlet of the passage, and the outlet, or the one-way valve radially extending within a cross section of the outlet and being arranged at the end of the passage or at the end of the passage opposed to the outlet.

IV. Capsule of one of the preceding items, wherein the capsule defining the passage further comprises an inlet at another end of the passage opposed to the outlet as well as a fluid permeable, non-dissolvable retainer, the retainer being arranged between the composition and the inlet of the capsule to block any flow of the composition through the retainer towards the inlet.

V. Capsule of one of the preceding items, wherein the passage is formed by the inner surface of a wall forming the capsule, the capsule further comprising support elements for supporting the dissolvable blocking element in the passage, the support elements comprising: an inner surface of the wall, a section of the wall tapering towards the outlet, an expanded cross section of the conduit, non-dissolvable filters or rods radially extending form the inner surface of the wall as in the passage, a shoulder or an elevation of the wall extending into the passage or a combination thereof, or wherein the at least one moveable lid is an integral part of the capsule, the at least one moveable lid being provided by a wall section of the capsule located at one end of the capsule, the wall section being cut to form the at least one lid.

VI. Capsule of one of the preceding items, wherein the capsule comprises an outlet part in which the dissolvable blocking element is fitted into, and an inlet part comprising a retainer attached to or fitted into the capsule in form of a filter and/or a grid formed of non-dissolvable material.

VII. Capsule of one of the preceding items, wherein the inner surface of the capsule enclosing the composition, except for the dissolvable blocking element, is formed of material being non-dissolvable in water, wherein the dissolvable blocking element is formed of water-dissolvable material, and wherein the one-way valve is formed of material being non-dissolvable in water or of water-dissolvable material.

VIII. Capsule of one of the preceding items, wherein the dissolvable blocking element comprises at least one of: fibrous web, fabric, textile, porous solid, gas and/or liquid permeable membrane and a solid block with at least one longitudinal pressure compensation channel, and wherein the one-way valve is a duckbill valve formed of the at least one lid provided by a cut wall section of the capsule, the at least one lid comprising one or a plurality of mutually adjacent lids.

IX. Capsule of one of the preceding items, wherein the dissolvable blocking element or the at least one lid comprises polyethylene glycol, polylactic acid, water dissolvable cellulose, such as hydroxypropylmethyl cellulose, hydroxypropyl cellulose, hydrolysed gelatine or mannite or mixtures of two or more thereof, or wherein the at least one lid comprises at least one of a polymer, a thermoplastic, polyethene (PE), polypropene (PP), polystyrole (PS), polyvinylchloride (PVC), polyacrylnitrile (PAN), polyamide (PA), polyester (PES), polyacrylate, the at least one lid being provided in a thin sheet or wall with a thickness suitable for allowing bending and opening of the at least one lid upon application of a vacuum equivalent to conventional suction movements to the outlet.

X. Capsule of one of the preceding items, wherein the composition is provided in the form of particles having a minimum particle size, the minimum particle size being provided to ensure the blocking of delivery of the composition to the outlet, the minimum particle size being larger than a pore size, a channel cross section, a channel diameter or a mesh size provided by the fluid permeable blocking element.

XI. Capsule of one of the preceding items, wherein the blocking element is comprised of a dissolvable material and provides structure, the combination of the material and the structure providing a dissolving rate of at least 30%, at least 50%, at least 60%, at least 70%, at least 80%, at least 90%, at least 95% or at least 99% of weight percent for a total immersion in water at 20° C. and 1013 hPa for a duration of at most 30 s, 20 s, 10, 5 s, 3 s or 2 s, wherein the dissolvable material is pharmaceutically acceptable.

XII. Capsule of one of the preceding items, comprising an outlet outer wall section at the outlet, the outer wall section forming a complementary connection element adapted to engage with an extension conduit, the extension being adapted to be sealingly attached to the complementary connection element, to the outlet or to the passage.

XIII. Package comprising a plurality of the capsules according to one of the preceding items, the package comprising a reclosable container containing the capsules or at least one blister package, the blister package defining individual storages each containing one capsule which can be retrieved from the individual storage by opening the individual storage, wherein the package preferably comprises an additional straw, mouthpiece of extension having an opening adapted to receive a plug-in part of the capsule, the plug-in part comprising the outlet.

XIV. Method for releasably sealing a capsule defining a passage comprising a composition to be orally administered, comprising the steps of:
providing a capsule with an inlet and an outlet being connected by the passage;
occluding the passage with a blocking element, the blocking element comprising a dissolvable blocking element of dissolvable material and having a fluid permeable structure or comprising a one-way valve as a part of the capsule; and
filling composition into a composition chamber within the passage.

XV. Use of a capsule according to one of items I-XII for the administration of a medicament or solid particles comprising a pharmaceutical preparation.

XVI. Use of a capsule according to one of items I-XII for taste-masked administration of a composition to be administered.

XVII. Method for oral application of a composition to be orally administered, comprising the steps of:
providing a capsule with an inlet and an outlet connected by a passage, the capsule being formed of non-dissolvable material, the passage comprising the composition as well as a blocking element, the blocking element being arranged in the passage at the outlet to block delivery of the composition through the outlet of the passage and comprising a dissolvable blocking element or a one-way valve as a part of the capsule;
dissolving the dissolvable blocking element by dissolving the blocking element or applying a vacuum to the outlet suitable for opening the one-way valve;
opening a passage section between the composition and the outlet for the composition; and
applying the composition to a patient through the outlet and the opened passage.

XVIII. Method of item XVII, wherein dissolving the blocking element comprises: immersing the dissolvable blocking element or the capsule's inlet into a solvent or applying a solvent to the blocking element by drawing fluid through the inlet and the blocking element and by compensating the low pressure resulting therefrom by supplying the solvent into the passage through the inlet of the capsule.

DESCRIPTION OF THE DRAWINGS

The figures show exemplary embodiments of the invention.

DETAILED DESCRIPTION OF THE DRAWINGS

Figure 1:
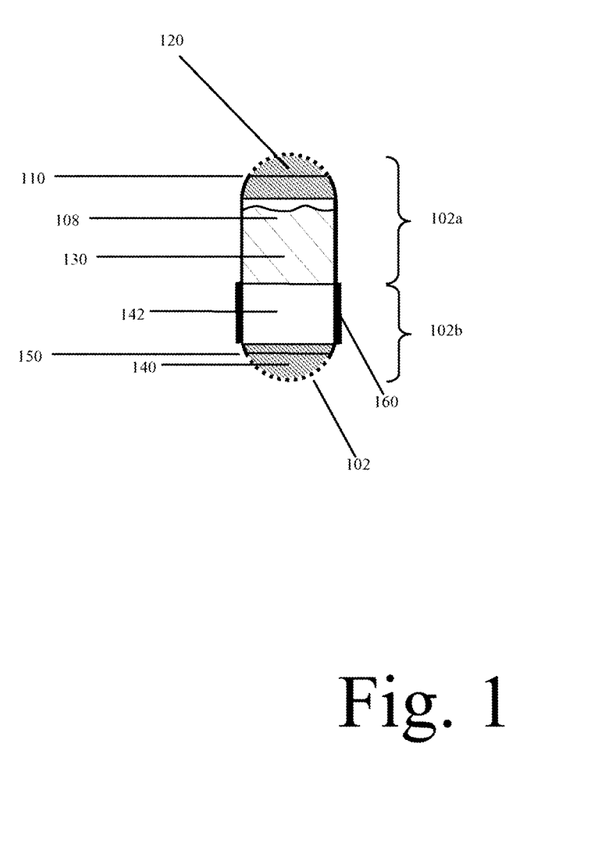
FIG. 1 shows a cross section of an embodiment of the capsule according to the invention.

FIG. 1 shows cross section of the preferred embodiment of the invention comprising a passage 108 within a capsule 102 which is adapted to be partly plugged into a conduit (not shown). The capsule is formed of an upper part or outlet part 102a and a lower part or inlet part 102b. The upper part comprises an outlet 110 formed as an opening in the upper part of the capsule 102a. The outlet 110 as well as the passage 108 is blocked by a dissolvable blocking element 120 (shown as dashed area). The blocking element extends in the capsule and partly extends through the outlet and in a volume outside the capsule adjacent to the outlet 110. The blocking element 110 encloses composition 130 located in the upper part 102a of the capsule. The lower part of the capsule 102b comprises a retaining element 140 (or retainer). The retaining element 140 obturates an inlet 150 of the capsule. The retainer 140 (as well as an optional filling element 142 integrally formed therewith) are provided in the complete lower part 102b of the capsule. The retaining element is provided as a porous sponge or filter. Further, the upper part 102a is engaged with the lower part 102b by means of an engaging element (not shown). Further, the lower part 102b comprises a thicker outer cross section 160 to avoid the lower part of the capsule entering the extension conduit 104. The upper part 102a has an outer cross section corresponding to the inner cross section of the extension conduit 104 such that only the upper part 102a extends into the extension conduit. The upper part 102a is attached to the inner wall of the respective end section of the extension conduit 104 by press-fit. Preferably, a snap-in connection is formed by two complementary connection elements, one of which is located at the upper part 102a and one of which is located at the lower part. Upon engagement, the parts are connected with each other by a snap connection.

An extension conduit (not shown) connectable to the capsule and in particular the outer wall of the conduit can comprise a gripping section as well as a mouthpiece section (opposed to the respective end section of the extension conduit 104) of the oral delivery system. Since the embodiment shown in FIG. 1 comprises the outlet 110 of the capsule, the outer wall of the outlet 110 and the outlet part 102a can be connected to the extension conduit comprising a mouthpiece adapted to be used by a patient.

The non-dissolvable elements, e.g. the upper part 102a and the lower part 102b have an impermissible structure formed of gelatine, starch or modified starch or other pharmaceutically acceptable materials. In particular, the same materials can be used to provide the upper part and the lower part of the capsule as are used for the blocking element, if the structure of the capsule, i.e. the side wall of the passage is impermissible and does not dissolve as rapid as the blocking element. In particular, if the upper and lower part of the capsule form smooth inner walls, the surface area is relatively small (in comparison to the dissolvable blocking element). This provides a time duration between the first contact with water and substantial structural degradation, which is substantially longer than the time duration of the blocking element between the first contact with water and substantial structural degradation the blocking element resulting in the release of the pharmaceutical composition (given that the contact with water is continuous).

In FIG. 1, the walls of the capsule, i.e. the sidewalls forming the upper part 102a and the lower part 102b a drawn in continuous lines and the contour of the capsule at inlet and outlet is shown in dashed lines. At the continuous lines, the upper and the lower part have continuous, impervious sidewalls forming the passage for directing the liquid flow. At the dashed lines, i.e. at the inlet and outlet, the capsule is pervious for gas and liquid to enable a flow from the inlet to the outlet (and to the space beyond the outlet), if e.g. vacuum is applied to the outlet. Preferably, the capsule provides a low flow resistance at the area shown with dashed lines such that liquid and gas can be flow from the space below the inlet (e.g. a glass with a drink) to the space above the outlet (e.g. a extension conduit in form of a straw or the patient's mouth). Parts shown with continuous lines (e.g. the side wall) provide features that do not provide a fluidic flow but direct the flow along the extension of the features, i.e. a fluidic flow from the capsule's inside to the space outside the capsule. At the parts shown with dashed lines, the capsule enables a fluidic flow through the features depicted with the dashed line (e.g. openings providing inlet and outlet), i.e. a fluidic flow from the capsule's inside to the space outside the capsule. Features shown with dashed lines allow gas or liquid flow.

Figure 2:
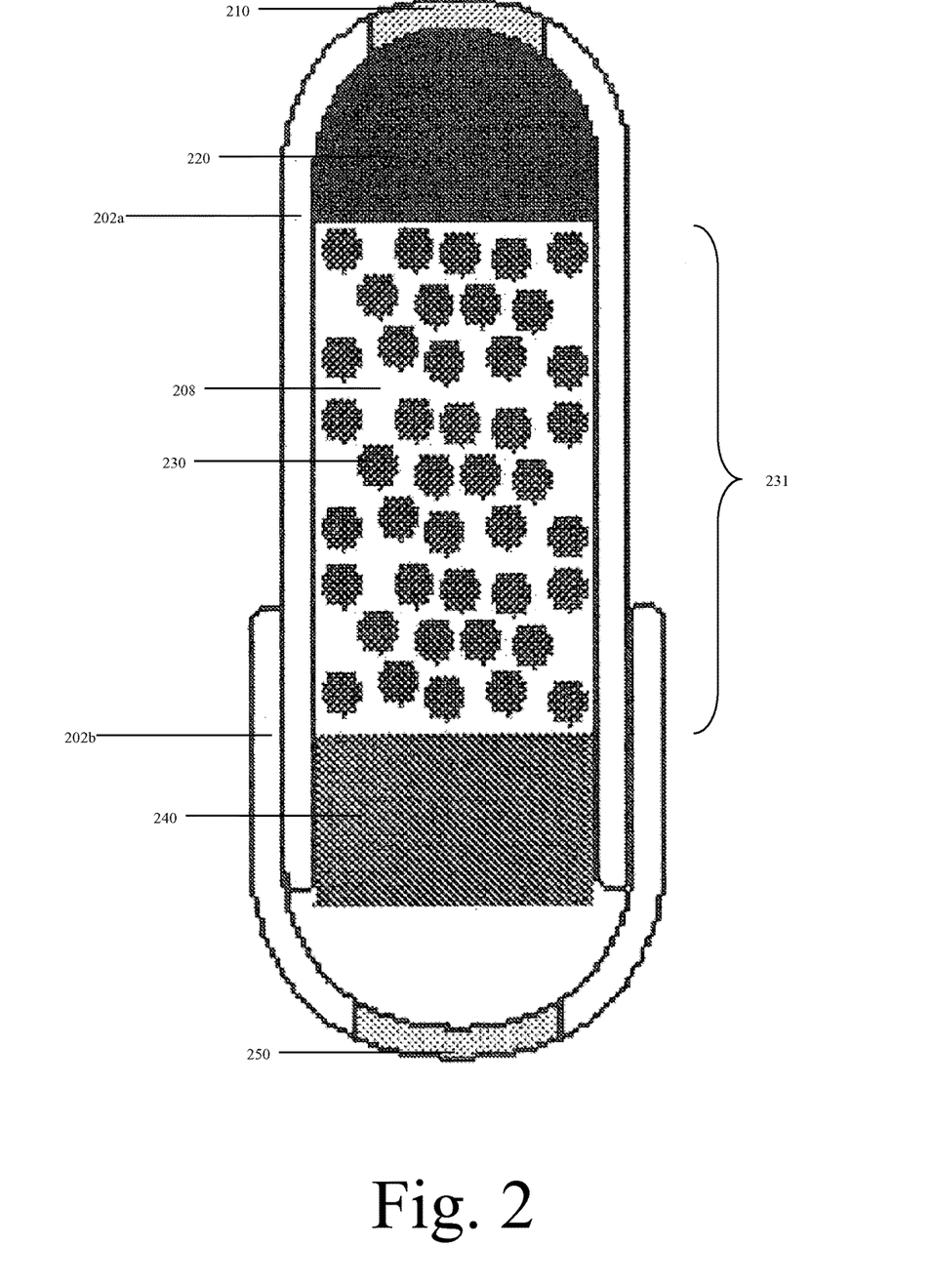
FIG. 2 shows a cross section of another embodiment of the capsule according to the invention suitable for explaining the manufacturing process.

FIG. 2 shows a capsule formed of two parts, an inlet part 202a and an outlet part 202b. The outlet part comprises an outlet opening 210 which is obstructed by a dissolvable blocking element 220. The outlet part extends between the outlet 210 and the position of the capsule, at which the tapering at the inner part begins. The inlet part comprises an inlet 250 similar or comparable to the outlet 210 both being provided by a hole in the wall of the capsule part. In FIG. 2, the openings providing the inlet and the outlet are shown as dotted area (=features enabling a flow). It can be seen that the diameter of the opening providing the inlet is greater than the diameter of the opening providing the outlet. Since the outlet part partly extends into the inlet part, the parts are connected with each other by friction. Preferably, a step connection is provided by mechanical connection elements at the inlet part and the outlet part of the capsule at the capsule section, in which the inlet part and the outlet part coextend along the longitudinal axis of the capsule.

The embodiment of FIG. 2 further comprises a retaining element 240 at the end of the outlet part, which is opposed to the inlet. In this way, manufacturing can be carried out by first preparing the outlet part followed by catching the inlet part 202b into the outlet part 202a. Between retainer 240 and blocking element, a composition 230 to be administered is enclosed. The capsule comprises a composition section 231 for accommodating the composition within walls of the capsule, i.e. the side walls of the outlet part of the capsule. One end of the composition section 231 abuts to the retaining element 240 and the opposed end of the other of the composition section 231 abuts to the blocking element 220. The composition is provided in particles with a minimum particle size, whereas the retainer is provided as a porous element, having pores which are smaller than the particle size of the composition. In the same way, the porous size of the blocking element 220 is smaller than a minimum particle size of the composition 230. In FIG. 2, the dark dotted area is filled by the dissolvable blocking element 220, whereas the lighter dotted area is filled with the retaining element 240.

A manufacturing process for providing the capsule of FIG. 2 comprises the following steps: separating the upper part from the lower part, if delivered capsules are in form of closed capsules, opening the closed ends of each part by drilling (or by cutting). The outlet part is stuffed with the blocking element 220 in order to close the outlet 210 for the composition. Then, the composition (i.e. particles comprising the composition) is filled into the outlet part of the capsule. Preferably, this step as well as the step of introducing the blocking element is carried out when the outlet 210 forms the lower end, and the opposite end of the outlet part is arranged above the outlet 210. The stuffing as well as the filling of the composition is carried out by transporting the respective element or component to the open end of the outlet part, which is opposed to the outlet 210. The retainer 240 is introduced into (at least a part of) the outlet part of the capsule, before, in a subsequent step, the inlet part of the capsule is pushed onto a part of the outlet part thereby closing the open end of the outlet part, which is opposed to the outlet 210. Again, preferably a part of or all steps of the manufacturing method as described above is carried out when the output part of the capsule is held upside down with reference to the orientation shown in FIG. 2.

In one embodiment, the manufacturing steps are carried out in the following sequence: providing both capsule parts, separating the capsule parts (if applicable); preparing the inlet and the outlet by opening the (closed) ends of both capsule in part (if applicable); instead of preparing: providing both parts comprising an inlet and an outlet (if applicable); introducing the blocking element into the outlet part and obstructing the outlet by the blocking element; introducing the composition; introducing the retaining element (sandwiching the composition between blocking element and retainer in the outlet part of the capsule); and closing the capsule by pushing the inlet part onto the outlet part, thereby engaging both parts in order to form a mechanical connection, e.g. a snap-in connection of connection elements provided by both parts of the capsule. Providing the inlet part with an opening in order to form the inlet can be carried out in any phase of the manufacturing and preferably before the inlet part engages the outlet part. In another embodiment of the manufacturing method, the blocking element, the composition and the retaining element are introduced into the capsule (preferably into the outlet part of the capsule) and the capsule is closed by connecting both parts with each other before inlet and outlet are provided into the wall of the inlet and the outlet part. In this embodiment, drilling or cutting the inlet and the outlet into the capsule's wall is performed after the introduction of the blocking element, the composition and/or the retaining element (or retainer) into the capsule or into a part or into both parts of the capsule.

Figure 3A:
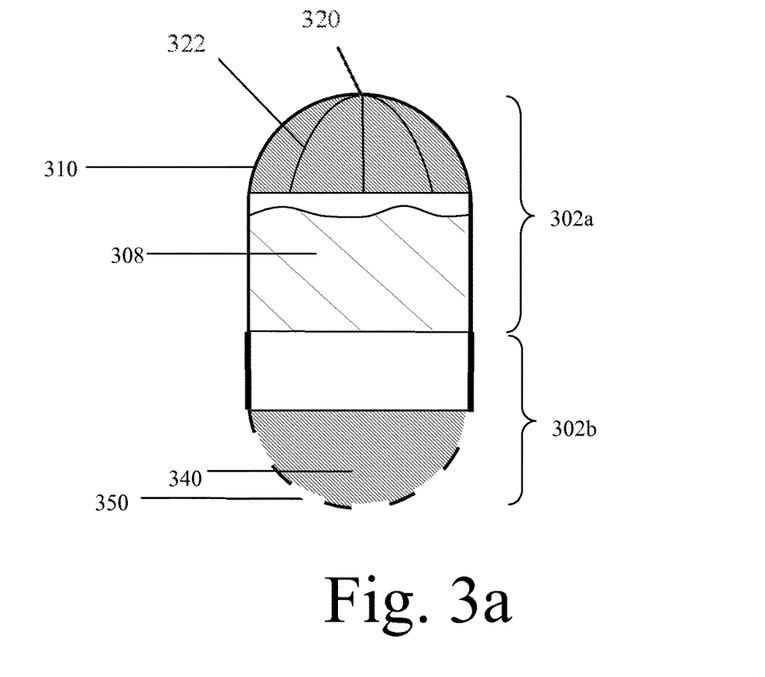
FIGS. 3a and 3b show an inventive capsule comprising a controllable blocking element in form of a one-way valve.

In FIG. 3a, a capsule according to the invention is shown having a controllable blocking element in form of a one-way valve 320. One-way valve 320 is an alternative to the blocking element 120 shown in FIG. 1, wherein blocking element 120 shown in FIG. 1 is a particular embodiment of the controllable blocking element. The capsule of FIG. 3a comprises an upper part 302a and a lower part 302b, similar to FIG. 1. The capsule of FIG. 3a is a two-part capsule, therein the upper and the lower part 302a,b comprise capsule halves, which are plugged together. The capsule of FIG. 3a comprises a retaining element 340, an inlet 350 and an outlet 310 at the one-way valve 320. Between retaining element 340 (similar to the retaining element 140 of FIG. 1) and controllable blocking element 320, a composition 308 is located within the capsule, such that upon entry of liquid into inlet 350, the liquid passes the retaining element, through the composition 308 and the outlet 310 provided by opened one-way valve 320. One-way valve 320 is opened by applying vacuum at the outlet 310. One-way valve 320 in closed condition (no vacuum) comprises slits or cuts 322 providing a gap smaller than the particles providing the composition. Thus, in closed condition, one-way valve 320 retains the composition 308 within the capsule.

One-way valve 320 is formed of the outer wall of the capsule at one end of the capsule. The outer wall of the capsule at this outlet end was formed of a closed end before cuts or slits 322 have been added. The slits 322 separate the outlet end 320 of the capsule into movable lids. The movable lids are moved by liquid passing through the outlet 310 towards the outside of the capsule thereby opening the gaps provided by the slits 322 such that the composition 308 can pass. In FIG. 3a, the capsule is shown on closed condition.

The movement of the lids upon opening is upwards (referring to the orientation given in FIG. 3a). The one-way valve 320 is provided by cutting a known pharmaceutical two-part capsule at the closed, curved end of one of its parts with equidistant cuts 322 along a line beginning at the apex of the curved end and towards the centre of the capsule, along a direction corresponding to the longitudinal axis of the capsule. In FIG. 3a, four cuts 322 (with a displacement of 45°, tangentially with respect to the longitudinal axis of the capsule) are given, each extending over the complete hemisphere formed by the curved end. This forms eight individual lids, which are individually movable. Any other number of lids can be provided, in particular more than two. Of course, azimuthal angles of less than 180° can be used, e.g. 160° or 150°. Preferably, the cuts 322 as well as the movable lids are axially symmetric with respect to the longitudinal axis of the capsule. The lids have a resilient force urging them together and providing only small slits or gaps 322 between neighbouring edges of the lids when vacuum pressure is absent to the outlet 320.

According to a preferred embodiment, the slits or gaps 322 between the lids are partly adhered together by a water dissolvable layer or dot, preferably located at the inside of the capsule, for example at a spot corresponding to the apex of the capsule. In this way, the obstruction provided by the lids is guaranteed until contact of the capsule with water, i.e. until liquid is drawn through the capsule. The layer or dot of water dissolvable material (e.g. sugar) immediately releases the lids at their respective apex allowing free movement of the lids. Such a water dissolvable layer or dot ensures that the lids obstruct the outlet for the composition, even if the composition is provided in small particles and the lids remain slightly opened (e.g. in case of very flexible lids).

Figure 3B:
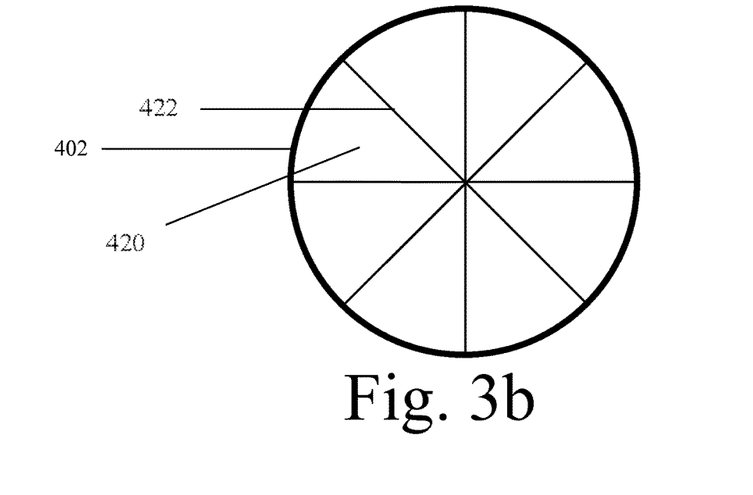

In FIG. 3b, the capsule of FIG. 3a is shown in top view. FIG. 3b shows the outlet 310 of FIG. 3a and in particular the one-way valve 310 of FIG. 3a. The one-way valve of FIG. 3b comprises lids 420 which are defined by symmetrical cuts 422. The lids 420 are based on an outer cylindrical part 402 of the capsule adjacent to the outlet, wherein the cylindrical part 402 is not cut and each of the lids form a spherical triangle one edge of which providing a hinge allowing (a part of) the movement of the lids 420. The one-way valve of FIG. 3b comprises eight similar lids and eight cuts starting from the apex extending radially outward (equivalent to four diametrical cuts with an offset of 45°). Only one of the lids and one of the cuts is depicted with a reference number for the sake of clarity. In an alternative embodiment (not shown), the cuts extend over less than complete hemisphere, e.g. starting at a height of reference sign 310 in FIG. 3a.

The invention claimed is:

1. A capsule suitable for releasably storing a composition to be administered, the capsule defining a passage, in which the composition to be administered is arranged, the capsule comprising:

a middle cut section having a substantially constant cross section and a tapered section at each end of the capsule;

a controllable blocking element in the form of a one-way valve, wherein the one-way valve is part of the capsule and comprises a plurality of movable lids obstructing an outlet of the passage at an end of the passage, the one-way valve providing a flow direction through the passage towards the outlet and blocking in the opposite flow direction, wherein the movable lids are an integrally formed part of the capsule, the moveable lids being provided by a wall section of the capsule located at one end of the capsule, the wall section having cuts to form the movable lids separated by the cuts; and an inlet at another end of the passage opposed to the outlet as well as a fluid permeable, non-dissolvable retainer, the retainer being arranged between the composition and the inlet of the capsule to block any flow of the composition through the retainer towards the inlet, wherein the ends of the capsule are hemispherical, the cuts being axially symmetric with respect to a longitudinal axis of the capsule, and the cuts start from an apex of the hemispherical end and extending radially outward.

2. The capsule according to claim 1, wherein the controllable blocking element is arranged between at least parts of the composition and the outlet, and/or the controllable blocking element is arranged to separate the composition from the outlet or from an external area next to the outlet.

3. The capsule according to claim 1, wherein the one-way valve radially extends within a cross section of the outlet and being arranged at the end of the passage or at the end of the passage opposed to the outlet.

4. The capsule according to claim 1, wherein an inner surface of the capsule enclosing the composition is formed of material being non-dissolvable in water, and wherein the one-way valve is formed of material being non-dissolvable in water or of water-dissolvable material.

5. The capsule according to claim 1, wherein the one-way valve is a duckbill valve formed of the movable lids provided by the cut wall sections of the capsule.

6. The capsule according to claim 1, wherein the movable lids comprises polyethylene glycol, polylactic acid, water dissolvable cellulose, or wherein the movable lids comprises at least one of a polymer, a thermoplastic, polyethene (PE), polypropene (PP), polystyrole (PS), polyvinylchloride (PVC), polyacrylnitrile (PAN), polyamide (PA), polyester (PES), polyacrylate, the movable lids being provided in a thin sheet or wall with a thickness suitable for allowing bending and opening of the movable lids upon application of a vacuum equivalent to conventional suction movements to the outlet.

7. The capsule according to claim 6, wherein the movable lids comprise hydroxypropylmethyl cellulose, hydroxypropyl cellulose, hydrolyzed gelatine or mannite or mixtures of two or more thereof.

8. A method for releasably sealing a capsule defining a passage comprising a composition to be orally administered, the method comprising the steps of:
providing the capsule according to claim 1;
occluding the passage with the blocking element; and
filling the composition into a composition chamber within the passage.

9. A method for oral application of a composition to be orally administered, the method comprising the steps of:
providing a capsule defining a passage, in which the composition to be administered is arranged, the capsule comprising a controllable blocking element in the form of a one-way valve, wherein the one-way valve is part of the capsule and comprises a plurality of movable lids obstructing an outlet of the passage at an end of the passage, the one-way valve providing a flow direction through the passage towards the outlet and blocking in the opposite flow direction, wherein the movable lids are an integrally formed part of the capsule, the moveable lids being provided by a wall section of the capsule located at one end of the capsule, the wall section having cuts to form the movable lids separated by the cuts, and an inlet at another end of the passage opposed to the outlet as well as a fluid permeable, non-dissolvable retainer, the retainer being arranged between the composition and the inlet of the capsule to block any flow of the composition through the retainer towards the inlet, wherein the capsule comprises a middle section having a substantially constant cross section and a tapered section at each end of the capsule;
applying a vacuum to the outlet suitable for opening the one-way valve;
opening a passage section between the composition and the outlet for the composition; and
applying the composition to a patient through the outlet and the opened passage, wherein the ends of the capsule are hemispherical, the cuts being axially symmetric with respect to a longitudinal axis of the capsule, the cuts start from an apex of the hemispherical end and extending radially outward, the cuts separating a plurality of the movable lids, and the method further comprising opening one of the movable lids.

* * * * *